(12) United States Patent
Vischer (10) Patent No.: US 7,435,575 B2
(45) Date of Patent: Oct. 14, 2008

(54) METHOD FOR PROCESSING A NUCLEIC ACID SAMPLE BY OSCILLATING A CARTRIDGE, A SYSTEM AND A CARTRIDGE FOR PERFORMING SUCH A METHOD

(75) Inventor: Peter Vischer, Küssnacht am Rigi (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 494 days.

(21) Appl. No.: 11/099,107

(22) Filed: Apr. 4, 2005

(65) Prior Publication Data
US 2005/0170496 A1 Aug. 4, 2005

Related U.S. Application Data

(62) Division of application No. 10/033,424, filed on Dec. 27, 2001, now Pat. No. 6,921,639.

(51) Int. Cl.
*C12M 3/00* (2006.01)
*C12M 1/34* (2006.01)

(52) U.S. Cl. .................................... 435/287.2; 435/6
(58) Field of Classification Search .............. 435/287.2, 435/6; 422/64
See application file for complete search history.

(56) References Cited

U.S. PATENT DOCUMENTS

| | | | |
|---|---|---|---|
| 5,133,937 A | | 7/1992 | Frackleton et al. |
| 5,959,098 A | * | 9/1999 | Goldberg et al. ........... 536/25.3 |
| 5,961,930 A | | 10/1999 | Chatterjee et al. |
| 6,589,740 B2 | | 7/2003 | Nakao et al. |
| 6,872,566 B2 | * | 3/2005 | Vischer et al. ........... 435/287.2 |
| 6,921,639 B2 | * | 7/2005 | Vischer .................... 435/6 |
| 2002/0164619 A1 | | 11/2002 | Vischer et al. |
| 2003/0059341 A1 | | 3/2003 | Gazeau |

FOREIGN PATENT DOCUMENTS

EP 0695941 A2 5/1995

(Continued)

*Primary Examiner*—Walter D. Griffin
*Assistant Examiner*—Shanta G Doe
(74) *Attorney, Agent, or Firm*—Townsend and Townsend and Crew LLP (57) ABSTRACT

A method for processing a nucleic acid sample contained in a liquid comprises: (a) introducing the liquid into a chamber (11) of a cartridge (12) which contains a chip shaped carrier (14), an active surface (15) of which carries an array of oligonucleotides; (b) positioning cartridge (12) into a cartridge holder (16) which holds cartridge (12); and (c) oscillating cartridge holder (16) and thereby cartridge (12) about an axis of rotation which is perpendicular to a vertical plane, thereby moving cartridge (12) back and forth between a first angular position (26) and a second angular position (28) which lie on opposite sides of an intermediate angular position (27) at which active surface (15) of chip shaped carrier (14) is at the lowest part of its motion path caused by the oscillating motion of cartridge (12). These oscillations cause a relative motion of the sample containing liquid contained in channel (13) with respect to active surface (15) of chip shaped carrier (14). Chamber (11) has a narrow interior and includes a curved channel (13). Chip shaped carrier (14) is located in a central zone of the curved channel (13).

4 Claims, 9 Drawing Sheets

FOREIGN PATENT DOCUMENTS

| | | |
|---|---|---|
| WO | WO 97/39151 | 10/1997 |
| WO | WO 99/03589 | 1/1999 |
| WO | WO 99/38612 | 8/1999 |
| WO | WO 99/41007 | 8/1999 |
| WO | WO 02/42775 A2 | 5/2002 |

* cited by examiner

METHOD FOR PROCESSING A NUCLEIC ACID SAMPLE BY OSCILLATING A CARTRIDGE, A SYSTEM AND A CARTRIDGE FOR PERFORMING SUCH A METHOD

CROSS REFERENCES TO RELATED APPLICATIONS

The present application is a divisional of U.S. application Ser. No. 10/033,424 filed Dec. 27, 2001 now U.S. Pat. No. 6,921,639 which is herein incorporated by reference in its entirety.

FIELD OF THE INVENTION

The present invention relates to a method for processing a nucleic acid sample contained in a liquid.

The invention further relates to a system for processing a nucleic acid sample contained in a liquid.

The invention further relates to a cartridge for processing a nucleic acid sample contained in a liquid.

The invention relates in particular to processing of a nucleic acid sample contained in a liquid introduced into a cartridge containing a chip shaped carrier having a biochemically active surface which is adapted to be read by an opto-electronic reading device.

BACKGROUND OF THE INVENTION

Within the context of the instant invention a chip shaped carrier is a substrate, in particular a glass chip of e.g. squared shape having a thickness of e.g. 0.7 or 1.0 millimeter and a so called active surface, which is a surface coated with an array of different snippets of DNA or other molecular probes, e.g. DNA oligonucleotide probes, located at known positions on that surface. Those probes serve for detecting DNA fragments with a complementary DNA sequence.

Within the context of the instant invention and in a preferred embodiment, the above-mentioned cartridge is in particular a cartridge made of a plastic material, which cartridge is used as a packaging device for packaging such a chip shaped carrier usually called DNA chip. More preferably, the cartridge is designed as a one-way cartridge.

DNA chips contained in such cartridges have a wide range of applications. For example, they may be used for understanding the structure-activity relationship between different biological materials or determining the DNA-sequence of an unknown biological material. For instance, the DNA-sequence of such unknown material may be determined by, for example, a process known as sequencing by hybridization. In one method of sequencing by hybridization, a sequences of diverse materials are formed at known locations on a surface of a chip, and a solution containing one or more targets to be sequenced is applied to that surface. The targets will bind or hybridize with only complementary sequences on the substrate. The locations at which hybridization occurs are detected with appropriate detection systems by labeling the targets with a fluorescent dye, radioactive isotope, enzyme, or other marker. Information about target sequences can be extracted from the data obtained by such detection systems.

By combining various available technologies, such as photolithography and fabrication techniques, substantial progress has been made in the fabrication and placement of diverse materials on chips of the above mentioned kind. For example, thousands of different sequences may be fabricated on a single substrate of about 1.28 square centimeter in only a small fraction of the time required by conventional methods.

Such improvements make these substrates practical for use in various applications, such as biomedical research, clinical diagnostics, and other industrial markets, as well as the emerging field of genomics, which focuses on determining the relationship between genetic sequences and human physiology.

For efficient use of a chip shaped carrier of the above described type it is necessary that the sample solution containing one or more targets to be sequenced effectively contacts the active surface of the chip shaped carrier. Moreover, in view of the relatively large number of sample solutions to be processed, this effective contact should be achieved with high reproducibility and at low cost.

Known prior art attempts to attain these aims require means for pumping a liquid containing a nucleic acid sample into and out a chamber of a cartridge in order to obtain the desired effective contact between the liquid containing the sample and the active surface of the chip shaped carrier. This approach is too expensive, cumbersome and requires too much working space, and can therefore not satisfy present day requirements on this kind of apparatuses.

A main aim of the instant invention is therefore to provide a method, a cartridge and a system which make it possible to provide effective contact of a solution processed in a cartridge of the above mentioned kind with the active surface of the chip shaped carrier and this with a high reproducibility and at low cost.

SUMMARY AND MAIN ADVANTAGES OF THE INVENTION

According to a first aspect of the invention the above aim is achieved with a method according to claim 1, with a system according to claim 4, and with a cartridge according to claim 7. Features of preferred embodiments are defined by the dependent claims.

The main advantages of the invention are that it makes possible to achieve the above mentioned, desirable effective contact between the sample solution and the active surface of the chip shaped carrier with high reproducibility and with simple means which in turn makes possible to achieve all this at low cost. This latter advantage becomes very important when a plurality of cartridges each containing a liquid containing a sample have to be simultaneously processed.

SHORT DESCRIPTION OF THE DRAWINGS

Preferred embodiments of the invention are described hereinafter more in detail with reference to the accompanying drawings, wherein.

DETAILED DESCRIPTION OF PREFERRED EMBODIMENTS

Figure 1:
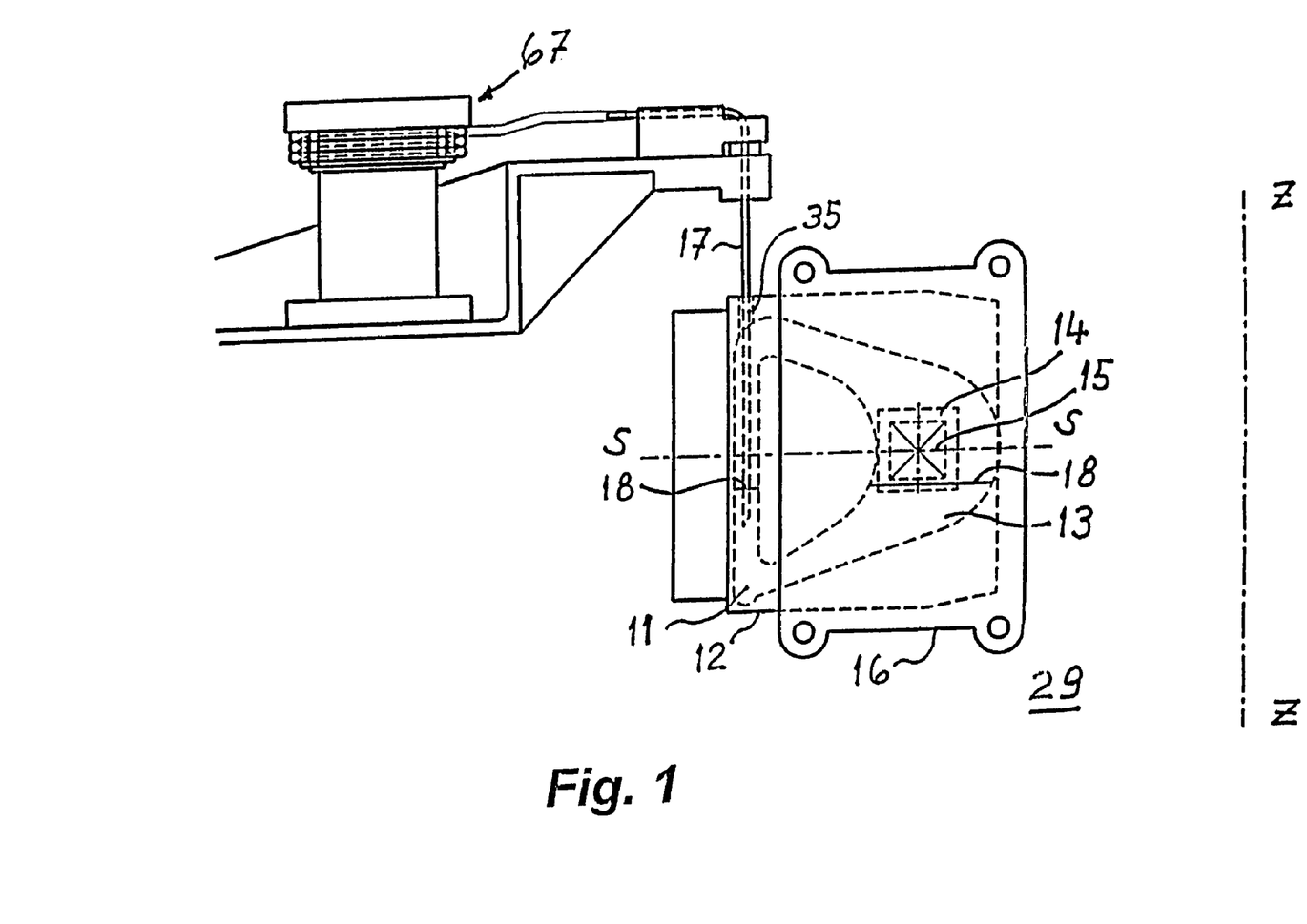
FIG. 1 shows a schematic representation of a cartridge 12 when it is being filled with a liquid containing a nucleic acid sample.

As schematically represented in FIG. 1, a cartridge 12 according to a first aspect of the invention comprises a chamber 11 which includes a curved channel 13. Cartridge 12 contains a chip shaped carrier 14 having an active surface 15 which carries an array of oligonucleotides and which faces an inner surface 24 of a channel plate 21, a part of cartridge 12 described hereinafter with reference to FIG. 2. Chip shaped carrier 14 is located in a central zone of channel 13. A portion of said channel 13 lies between active surface 15 of chip shaped carrier 14 and the inner surface 24 of a channel plate 21. In FIG. 1 line Z-Z is a vertical straight line.

FIG. 1 shows cartridge holder 16 and cartridge 12 in a position 29 at which a mid-axis S-S of cartridge 12 lies in a horizontal plane and is thus perpendicular to line Z-Z.

FIG. 1 shows just one possible cartridge position which is suitable to introduce liquid into the cartridge or to remove liquid from the cartridge. Another possible and even more preferable cartridge position for this purpose is one where the mid-axis S-S of the cartridge forms an angle greater than 90 degrees with an horizontal plane, e.g. an angle of 110 degrees. Such a position is more advantageous for removing liquid from the channel of the cartridge, because its lower arm becomes more inclined.

With cartridge 12 in the position shown in FIG. 1, a predetermined volume of a liquid containing a nucleic acid sample is introduced into chamber 11 through an opening 35 of cartridge 12 by means of a pipetting needle 17 which is part of an automatic pipetting unit 67 which is only partially represented in FIG. 1. Opening 35 is used as inlet and outlet of cartridge 12. The level reached by the sample containing liquid in chamber 11 is represented in FIG. 1 by horizontal line segments 18.

An advantage of the cartridge design represented in the enclosed drawings and of the initial position chosen for introducing a liquid containing a sample into the cartridge is that when a liquid is introduced into the cartridge as described above, the liquid initially remains below the lower edge of the chip shaped carrier 14. This makes possible to choose the point of time at which the binding reaction between the sample contained in the liquid and the active surface of the chip shaped carrier starts by choosing the point of time at which the oscillation movement of the cartridges is started.

Figure 2:
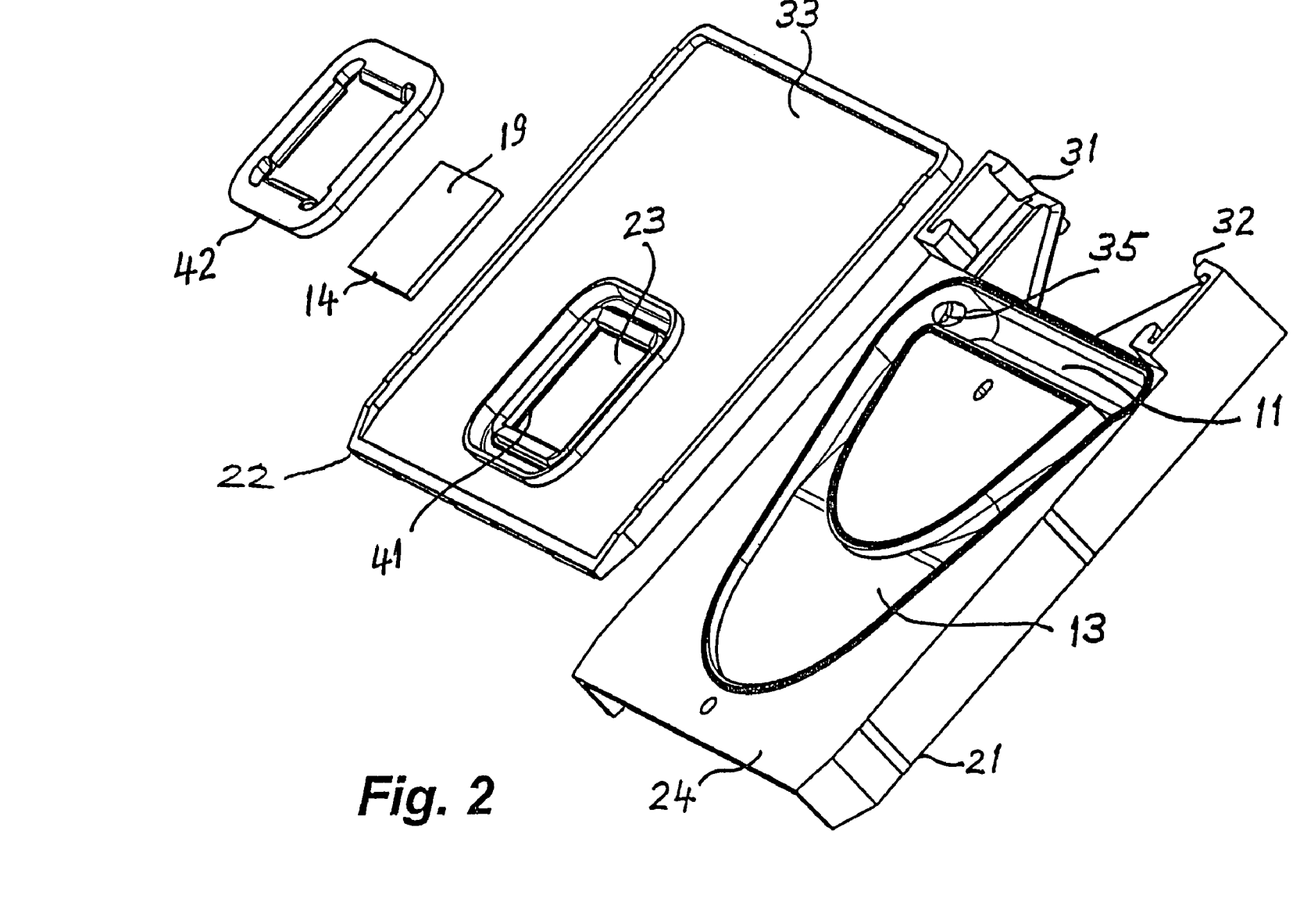
FIG. 2 shows an perspective exploded view of components of cartridge 12 showing in particular the interior of chamber 11 and channel 13 formed in a channel plate 21 which is part of cartridge 12.
Figure 3:
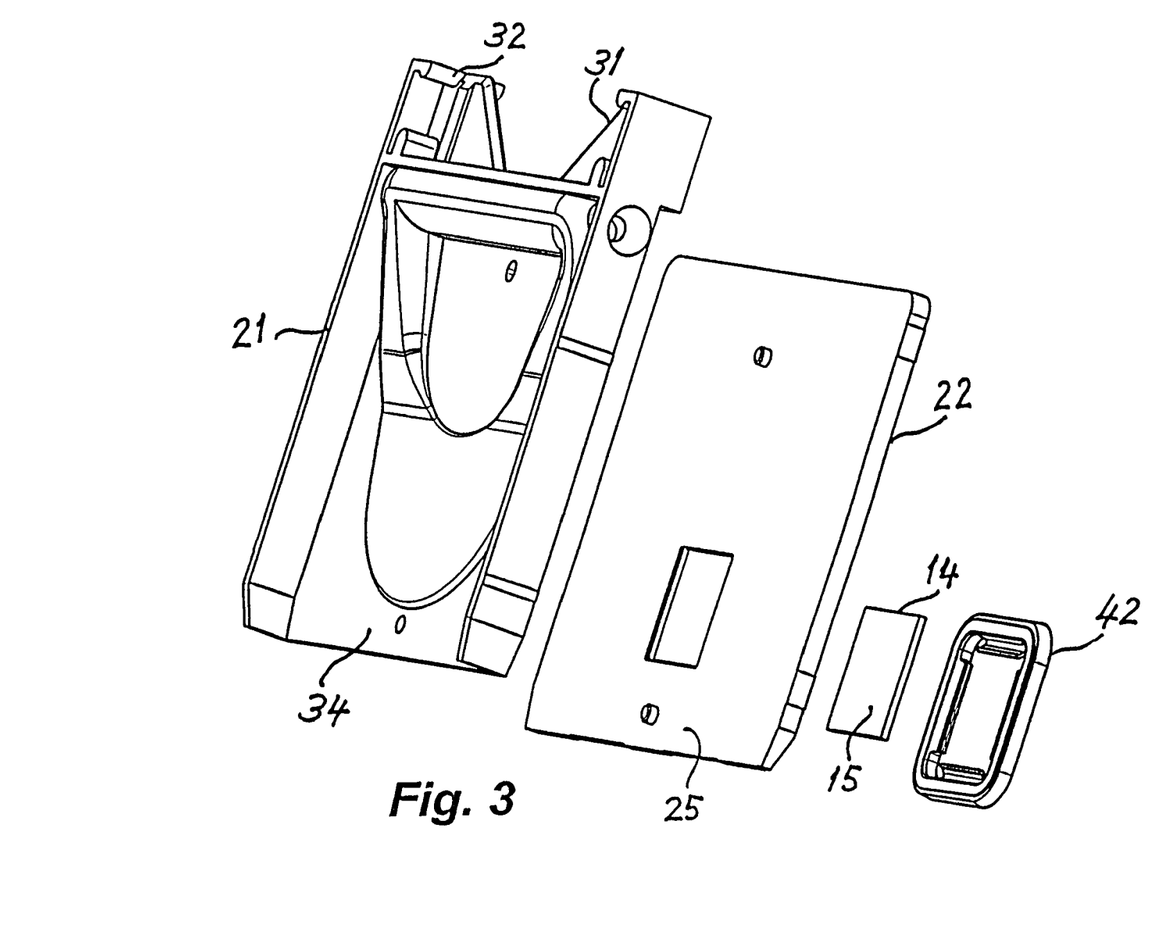
FIG. 3 shows an perspective exploded view of components of cartridge 12 seen from a point of view opposite to the one of FIG. 2 and showing in particular the inner surface of a chip plate 22 which is part of cartridge 12 and an active surface 15 of a chip carrier plate 14.

As shown more in detail by the perspective views shown by FIGS. 2 and 3, cartridge 12 comprises the following components: a channel plate 21 which comprises and substantially defines the shape of chamber 11 and of channel 13, and a chip plate 22 which is adapted to receive and hold chip shaped carrier 14 within a cavity 23 of chip plate 22. Channel plate 21 and chip plate 22 are so configured and dimensioned that they are adapted to be assembled together to form cartridge 12.

FIG. 2 shows the following parts of cartridge 12: the inner surface 24 of channel plate 21, the interior of chamber 11 and channel 11 formed in channel plate 21, opening 35 of channel plate 21 which is used as an inlet and outlet of cartridge 12, the outer surface 33 of chip plate 22, the interior of cavity 23 of chip plate 22 and the back side surface 19 of chip shaped carrier 14 which lies on the opposite side of the active surface 15 thereof.

FIG. 3 shows the following parts of cartridge 12 not shown by FIG. 2:

the inner surface 25 of chip plate 22, the active surface 15 of chip shaped carrier 14, and the outer surface 34 of channel plate 21.

Channel plate 21, chip plate 22 and other parts of cartridge 12 are made preferably of plastic materials which are suitable manufacture by injection molding and also for carrying out the envisaged process steps for processing a sample containing liquid of the above mentioned kind. Such plastic materials should be chemically inert so that they cannot interfere with the processing of the samples contained in such liquids. Moreover the material chosen for the manufacture of components of cartridge 12 should not be fluorescent, so that they cannot interfere with fluorescence measurements usually performed after processing e.g. a nucleic acid sample contained in a liquid. Channel plate 21 and chip plate 22 can but must not necessarily be transparent.

As shown by FIGS. 2 and 3, the upper part of channel plate 21, where opening 35 is located, comprises projections or tongues 31, 32 which are integral parts of cartridge 12 and which are so configured and dimensioned that they are adapted to be grasped by a suitable gripper of a transport device in order to transport and insert a cartridge 12 into a cartridge holder 16 and to remove a cartridge 12 from a cartridge holder 16.

The process of manufacture of cartridge 12 comprises positioning and fixing chip shaped carrier 14 into a corresponding cavity 23 available in chip plate 22 e.g. by means of a sealing frame 41 and a locking frame 42 and by assembling together channel plate 21 and chip plate with carrier 14 attached to it in order to form a cartridge 12 ready for use, wherein the active surface 15 of carrier is at the above mentioned position with respect to channel 13. The just mentioned assembling of channel plate 21 and chip plate 22 forms chamber 11 and channel 13 within cartridge 12.

The means for positioning and fixing chip shaped carrier 14 into cavity 23 available in chip plate 22 are preferably those described in co-pending European patent application No. 00810501.7 entitled "Device for packaging a chip shaped carrier and process for assembling a plurality of such carriers" filed on Jun. 8, 2000 by the applicant of this application.

Figure 4:
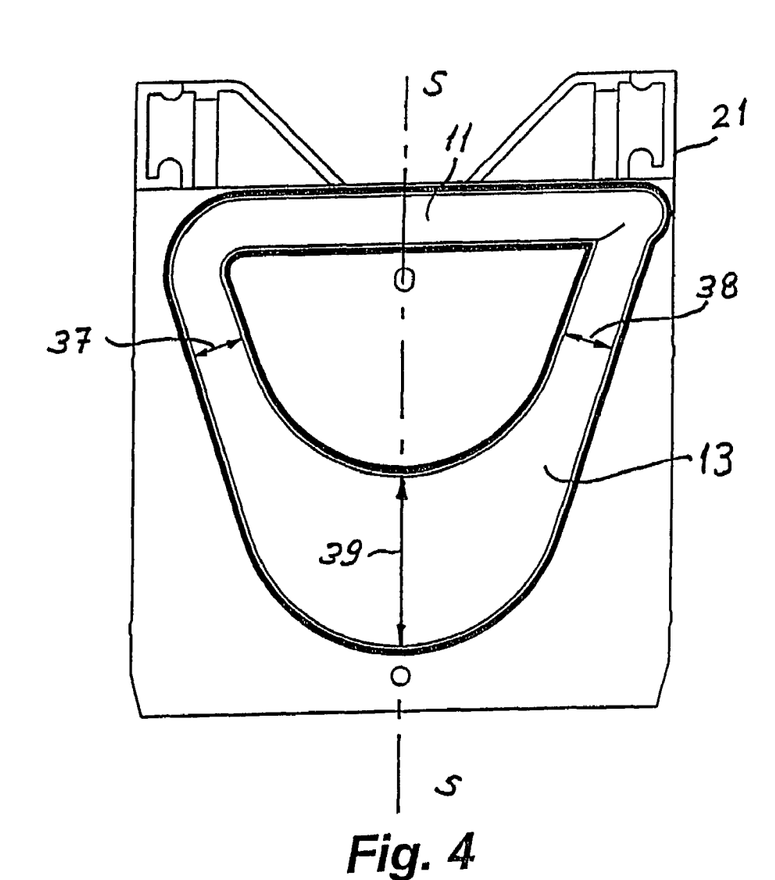
FIG. 4 shows a top view of the channel plate 21 of cartridge 12 and of channel 13 thereof.
Figure 5:
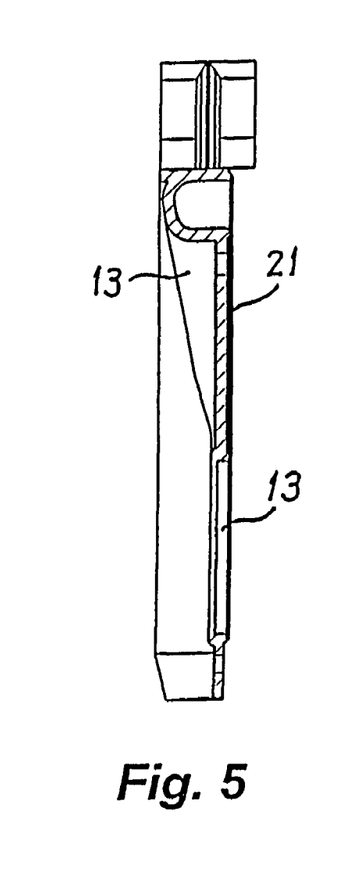
FIG. 5 shows a cross-sectional view of the channel plate 21 of cartridge 12 and of channel 13 thereof.

As shown more in detail by FIGS. 4 and 5, curved channel 13 has a variable width and a variable depth along its length. As shown by FIG. 4, the width 37 respectively 38, of the end segments of channel 13 is smaller than the width 39 of the central part of this channel, and the width of channel 13 continuously increases over a portion of channel 13 and reaches a maximum value at the center thereof. As shown by FIG. 5, the depth of channel 13 has a minimum value D1 over the central part thereof, whereas in the end segments of channel 13 (i.e. outside the central part thereof) its depth D2 continuously increases with increasing distance from the center of channel 13 and reaches a maximum value at the end segments of channel 13.

In a preferred embodiment of the invention the variation of the width and the depth of channel 13 along its length is so chosen and dimensioned that the cross-section of channel 13 remains fairly or at least approximately constant over its entire length or at least over a substantial part of its length. The relatively small value of the height (depth) of channel 13 yields a low Reynolds number and makes therefore possible to achieve a laminar flow of liquid within channel 13 when cartridge 12 is oscillated back and forth between two angular positions as described hereinafter. The advantageous effect of such a laminar flow is a very effective and reproducible contact between the nucleic acid sample contained in the liquid and the active surface 15 of chip shaped carrier 14.

An additional advantage which results from the combined choice of a channel 13 having a curved shape and having a substantially constant cross-section over its length is that it makes possible to make a compact cartridge 12 of relatively small dimensions, and this in turn makes it possible to accommodate a plurality of such cartridges in a compactly built apparatus.

As can be appreciated in particular from FIGS. 4 and 5, but also from FIGS. 2 and 3, chamber 11 has a narrow interior and includes a curved channel 13 which is formed within chamber 11. Chamber 11 and channel 13 are cavities comprised between inner surface 24 of channel plate 21 and inner surface 25 of chip plate 22. These inner surfaces are shown by FIG. 2 respectively FIG. 3 and are substantially opposite to each other. One of these inner surfaces is an inner surface 24 of channel plate 21 and the other is an inner surface 25 of chip plate 22.

Figure 6:
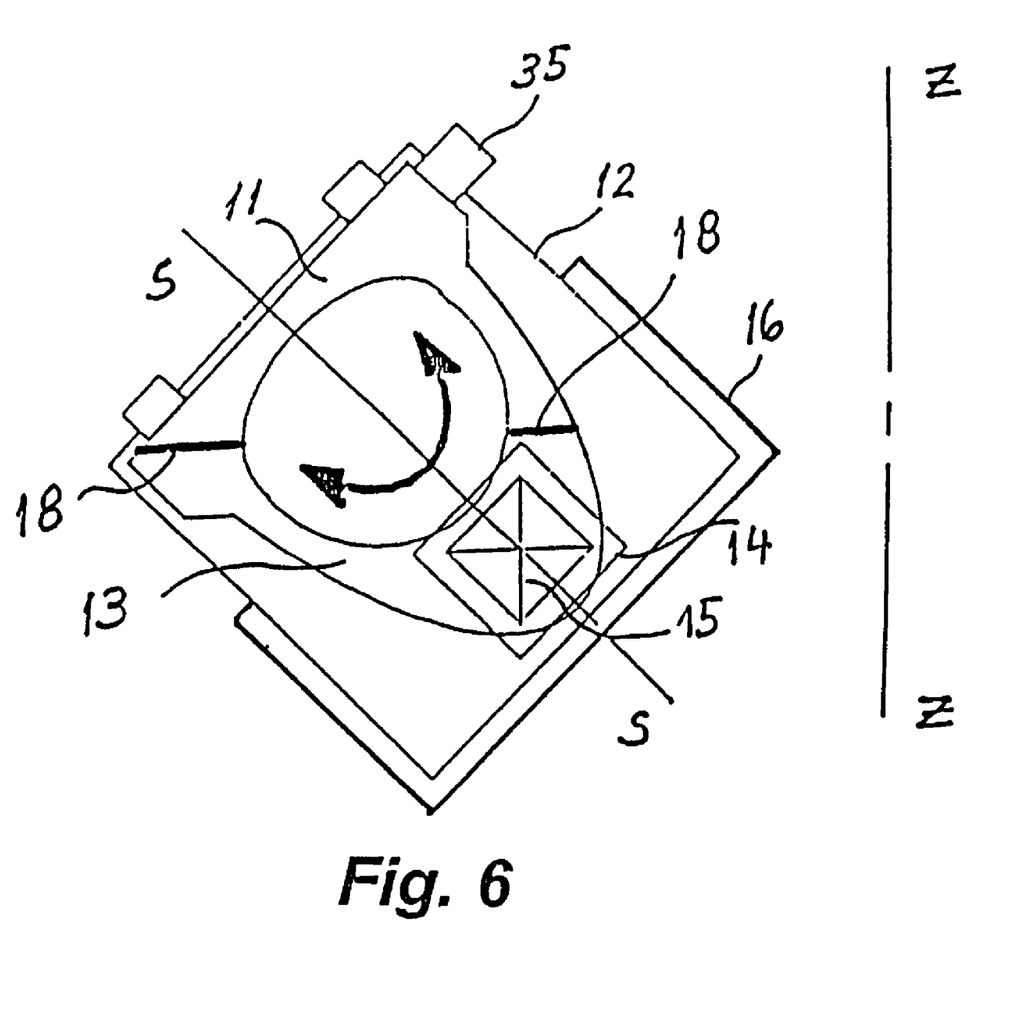
FIG. 6 shows cartridge 12 and cartridge holder 16 in a first angular position 26.
Figure 7:
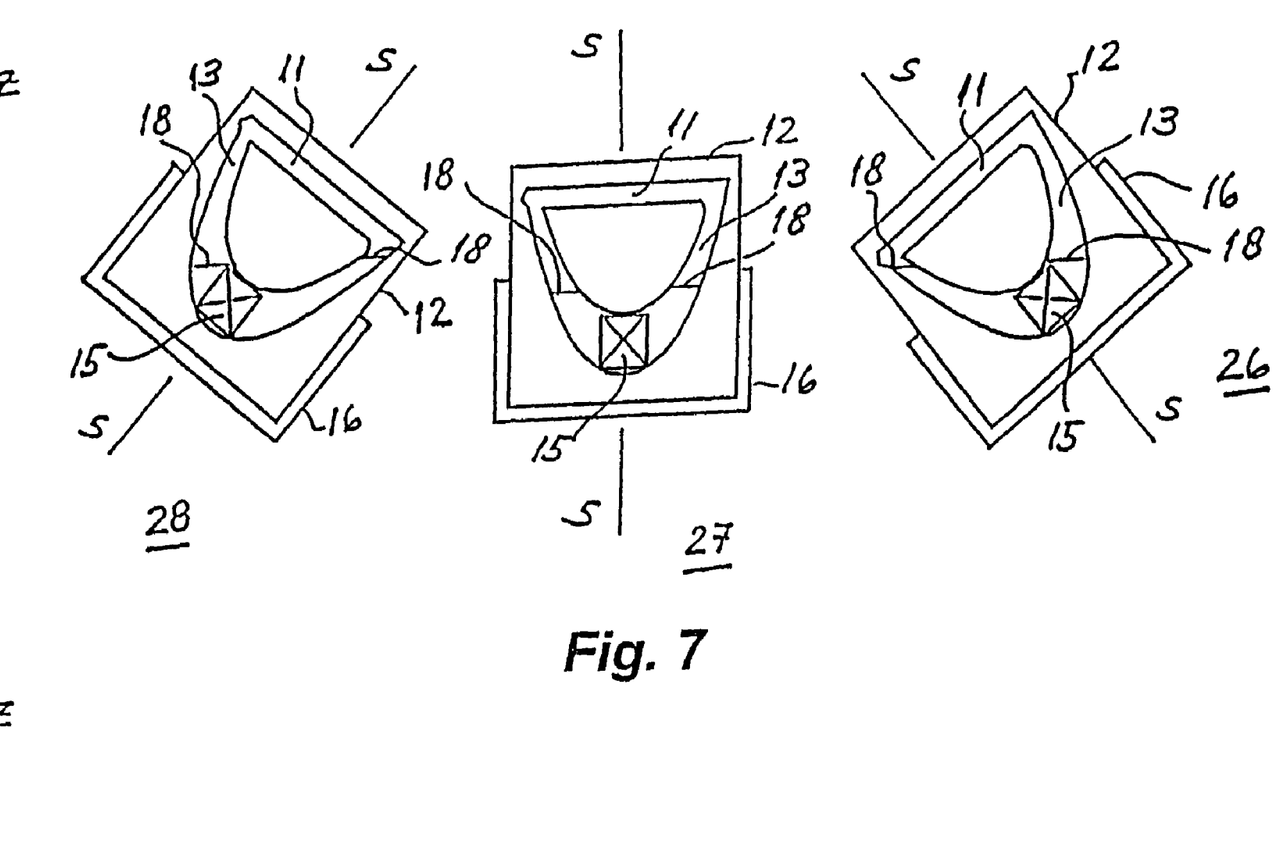
FIG. 7 shows different angular positions of cartridge 12.

In order to perform a method according to the invention, cartridge 12 is inserted and thereby positioned into a cartridge holder 16 which is represented schematically in FIGS. 1, 6 and 7.

Cartridge 12 and cartridge holder 16 are so configured that when cartridge 12 is positioned into cartridge holder 16 the active surface 15 of chip shaped carrier 14 preferably lies in a substantially vertical plane. However, the active surface 15 does not need to be vertical, it may also be inclined or even horizontal, even if these variants are expected to perform less well.

A system according to a first aspect of the invention comprises a cartridge 12 and a cartridge holder 16 having the above described features and comprises in addition means for oscillating cartridge holder 16 and thereby cartridge 12 about an axis of rotation which is substantially perpendicular to the above mentioned vertical plane.

The means for oscillating cartridge holder 16 are in particular adapted for moving cartridge holder 16 and thereby cartridge 12 back and forth between a first angular position 26 and a second angular position 28 shown in FIG. 7. During these oscillations the active surface 15 of chip shaped carrier 14 lies in a substantially vertical plane. FIG. 6 also shows cartridge 12 in first angular position 26.

FIG. 7 shows different angular positions of cartridge 12. As can be appreciated from FIG. 7, angular positions 26 respectively 28 lie on opposite sides of an intermediate angular position 27 at which the active surface 15 of chip shaped carrier 14 is at the lowest part of its motion path during oscillation of cartridge holder 16 and thereby cartridge 12 back and forth between first and second angular positions 26 respectively 28. When cartridge 12 is oscillated in this way gravity force acting on the liquid contained in channel 13 of cartridge 12 maintains level 18 of the liquid in a horizontal plane and causes a relative motion of the sample containing liquid in channel 13 with respect to the active surface 15 of chip shaped carrier 14. This relative motion provides a very effective contact of that liquid containing the sample with the active surface 15 of chip shaped carrier 14.

In FIGS. 6 and 7 line Z-Z is a vertical straight line.

At the intermediate angular position of cartridge 12 its mid-axis S-S is in a vertical position and is thus parallel to line Z-Z. At the first angular position 26 of cartridge 12 its mid-axis S-S forms a positive angle with a vertical line parallel to line Z-Z. At the second angular position 28 of cartridge 12 its mid-axis S-S forms a negative angle with a vertical line parallel to line Z-Z.

In a preferred embodiment, first angular position 26 is located at an angle of about plus forty degrees with respect to the intermediate angular position 27, and second angular position 28 is located at an angle of about minus forty degrees with respect to the intermediate angular position 27. An angle smaller than plus/minus 40 degrees is even more preferable in order to reduce the size of the cartridge.

The means for oscillating cartridge holder 16 are also adapted for bringing cartridge holder 16 and thereby cartridge 12 to the angular position shown in FIG. 1 which is at an angle of ninety degrees with respect to the intermediate angular position 27 shown in FIG. 7. As mentioned above an angle larger than 90 degrees, e.g. 110 degrees, is also suitable and even more preferable.

The means for oscillating a cartridge holder 16 holding a single cartridge 12 are in principle very similar to those described hereinafter with reference to FIG. 8 for oscillating a cartridge holder 36 adapted for holding a plurality of cartridges 12.

Figure 8:
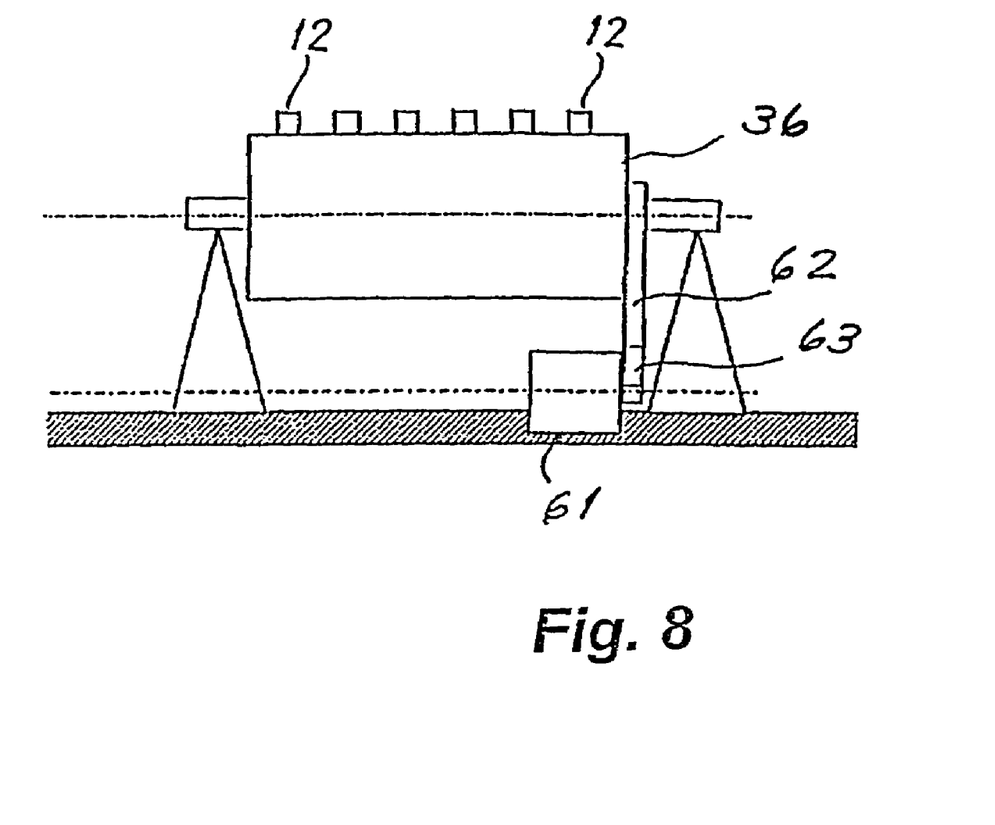
FIG. 8 shows a system according to the invention for handling a plurality of cartridges 12 simultaneously.

FIG. 8 shows a side view of a preferred embodiment of a system according to the invention. This embodiment comprises a cartridge holder 36 having a plurality of compactly arranged chambers each of which is adapted to receive and hold a cartridge 12, and a means for oscillating cartridge holder 56. This system is thus adapted to receive and hold a plurality of cartridges 12 and to oscillate them simultaneously in a similar way as described above for the case of a single cartridge holder 16.

Cartridges 12 and cartridge holder 36 are so configured that when cartridges 12 are positioned into cartridge holder 36 the active surface 15 of each chip shaped carrier 14 preferably lies in a substantially vertical plane. However, the active surface 15 does not need to be vertical, it may also be inclined or even horizontal, even if these variants are expected to perform less well.

Figure 9:
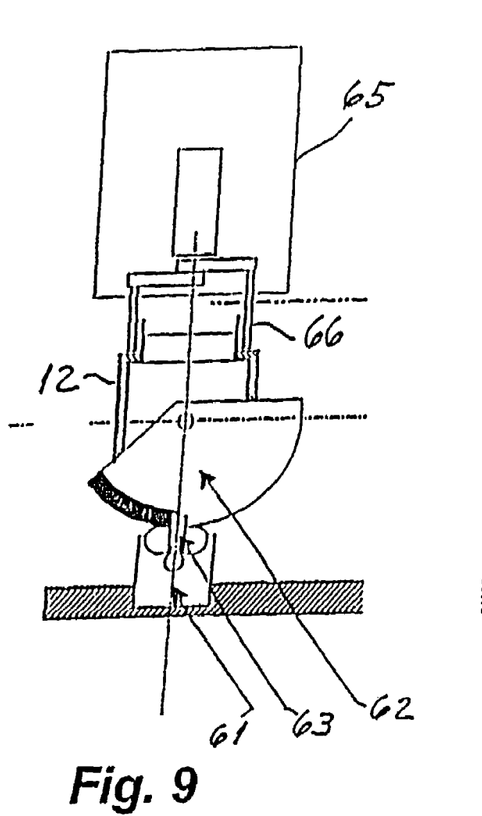
FIG. 9 shows a transport head which has a gripper 66 at the moment it positions a cartridge 12 into a cartridge holder.

FIG. 9 shows a transport head 65 which has a gripper 66 at the moment it positions a cartridge 12 into a cartridge holder 36 shown in FIG. 8. Also represented in FIG. 9 are means for oscillating cartridge holder 36 and thereby cartridges 12 positioned into that holder. These means include e.g. a step motor or a DC motor 61, drive means 62 and coupling means 63 located between motor 61 and drive means 62. Drive means 62 and coupling means 63 can include e.g. a serrated belt, a gearing, a friction drive or a steel band.

Figure 10:
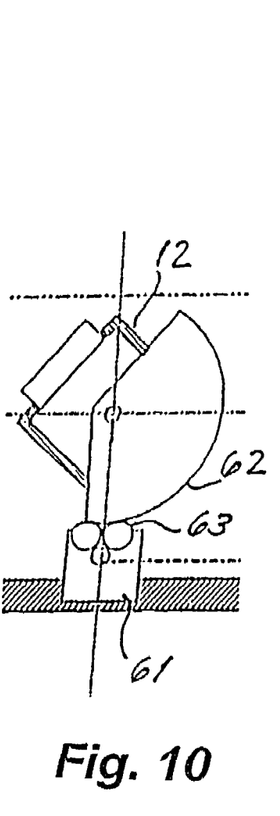
FIG. 10 shows a cartridge 12 in a first angular position 26.

FIG. 10 shows a cartridge 12 in a first angular position 26.

Figure 11:
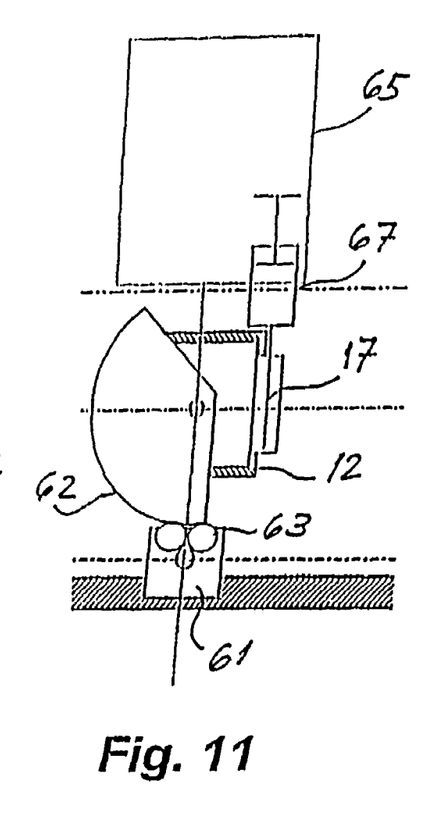
FIG. 11 shows a cartridge 12 in an angular position 29 which is the same as the one shown in FIG. 1.

FIG. 11 shows a cartridge 12 in an angular position 29 which is the same as the one shown in FIG. 1. Also represented in FIG. 11 is a part 67 of a pipetting unit. This part 67 is moved by means of transport head 65, which as mentioned above also carries and moves gripper 66. Part 67 of the automatic pipetting unit comprises pipetting needle 17 shown also in FIG. 1.

Figure 12:
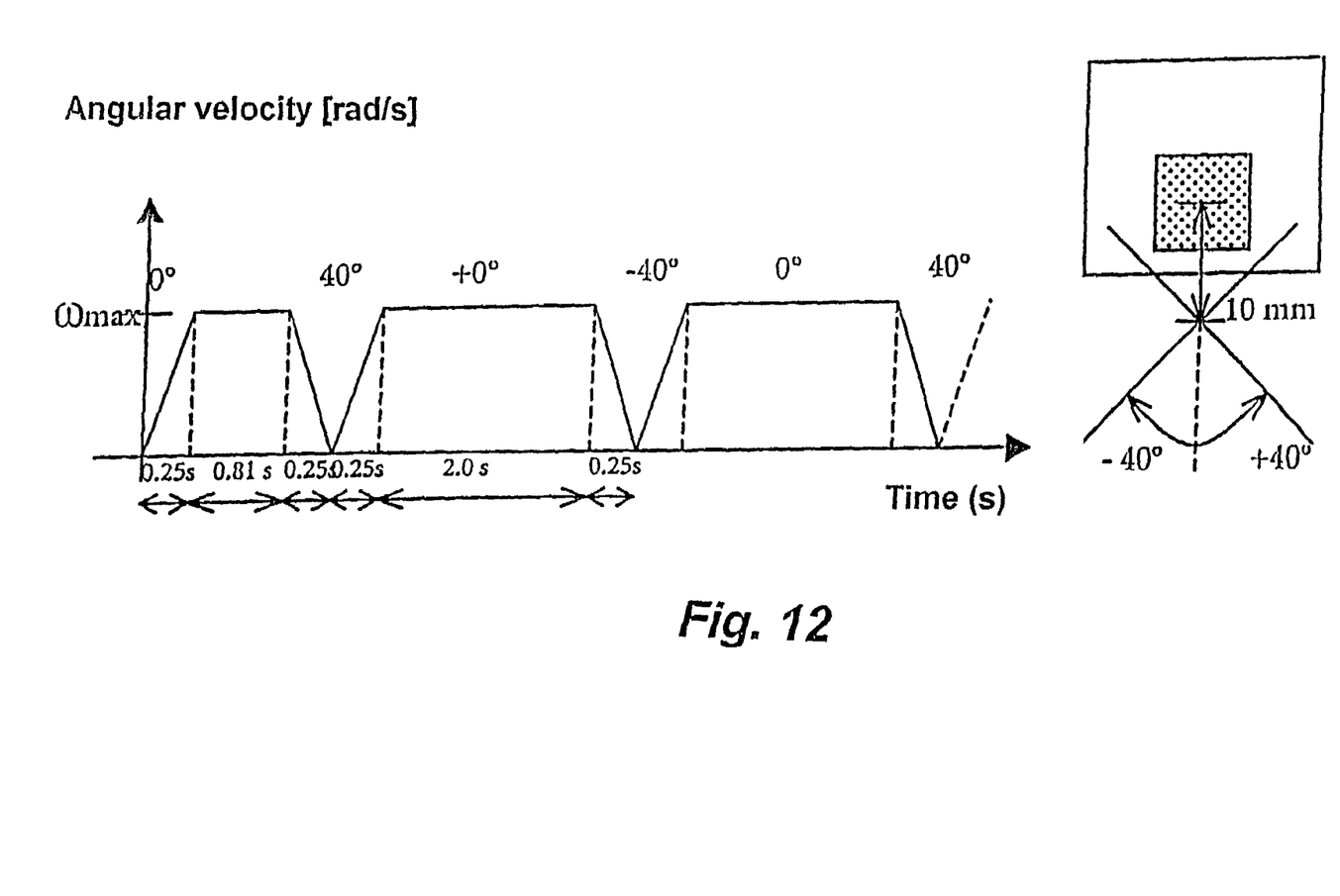
FIG. 12 shows a diagram of the variation of the angular velocity $\omega=d\theta/dt$ with time for oscillation movement of cartridge 12.

FIG. 12 shows as an example a diagram of the variation of the angular velocity $\omega = d\theta/dt$ with time which is achievable with the above described means for oscillating cartridge 12 for the case where the angle of oscillation varies between plus 40 degrees and minus 40 degrees. With the values shown in this diagram the oscillation frequency is 0.2 cycle per second and the maximal angular velocity is about 0.62 rad per second or 35.6 degrees per second. A cartridge oscillation according to the diagram of FIG. 12 is used for instance during the sample hybridization step described hereinafter. For the sample rinse step described hereinafter the variation of the angle of oscillation with time has a similar shape as in FIG. 12, but the oscillation frequency is e.g. of 0.4 cycle per second.

In a preferred embodiment, the function angle vs. time differs from the one shown by FIG. 12 and has approximately a sinusoidal shape in order that the movement parameters (location, velocity, acceleration) vary substantially smoothly.

A method for processing a nucleic acid sample contained in a liquid according to a first aspect of the invention can be carried out with the means described in this example and comprises the following steps:

(a) introducing a liquid containing a nucleic acid sample into chamber 11 of cartridge 12 and thereby into channel 13 formed within that chamber, (b) positioning cartridge 12 into cartridge holder 16 in such a way that active surface 15 of chip shaped carrier 14 lies in a substantially vertical plane, this positioning of cartridge 12 in cartridge holder 16 being effected before or after introduction of the liquid containing said sample into chamber 11, (c) oscillating cartridge holder 16 and thereby cartridge 12 about an axis of rotation which is substantially perpendicular to a vertical plane, thereby moving said cartridge 12 back and forth between first angular position 26 and second angular position 28 which lie on opposite sides of an intermediate angular position 27 at which active surface 15 of chip shaped carrier 14 is substantially at the lowest part of its motion path caused by the above mentioned movement of cartridge 12 in order to cause a relative motion of the liquid contained in channel 13 with respect to active surface 15 of said chip shaped carrier 14.

According to a preferred embodiment of the invention a method of the type just described is carried out simultaneously on a plurality of cartridges by means of a system according to the invention adapted for that purpose and comprising a cartridge holder 36 and the means for oscillating it shown in FIGS. 6 to 11.

A typical use of a method, cartridge and system according to the invention is for carrying out process steps of a so called post PCR processing of a nucleic acid sample which has been amplified by means of a PCR method or the like.

Such post PCR processing carried out using cartridge 12 includes in general terms the following steps: introducing liquid into chamber 11 and into channel 13 of cartridge 12 at some points of time and withdrawing liquid from chamber 11 and channel 13 of cartridge 12 at other points of time, repeating this steps several times, and heating and cooling cartridge 12 during predetermined time intervals according to predetermined temperature profiles, e.g. in a temperature range between zero and seventy degrees Celsius. The liquid containing a nucleic acid sample is one of the liquids introduced into and withdrawn from cartridge 12. Another type of liquid handled in this way as part of the method is e.g. buffer liquid used for rinsing chamber 11 and channel 13 during rinsing steps mentioned hereinafter.

More in detail a post PCR processing of an amplified nucleic acid sample using the devices described above comprises e.g. the following steps:

1) Introduction of the Amplified Nucleic Acid Sample into the Cartridge

A liquid containing this sample is introduced into cartridge 12 through an inlet thereof and by means of the pipetting needle of an automatic pipetting unit as shown by FIG. 1.

2) Sample Hybridization

During an hybridization step by means of heat transfer the temperature of the cartridge is maintained at a predetermined level. Over the whole duration of this step, which usually takes between 30 and 60 minutes, but which can take up to 8 hours (e.g. for a gene expression), a relative movement of the sample containing liquid with respect to the active surface of the chip shaped carrier and thereby a flow of that liquid over that surface is effected by the means described above. In connection with this step it is important to note that the chamber and the channel within the cartridge are so configured that a uniform distribution of the liquid over the active surface of the chip shaped carrier is achieved.

3) Sample Rinse

In a first washing step (rinse) the interior of cartridge 12 is rinsed with a washing buffer which flows into the cartridge through an inlet thereof and leaves it through an outlet thereof. This step is repeated up to ten times.

4) Rinse Incubation

This step serves for stabilizing the processing of the sample containing liquid contained in the cartridge. During this step which takes about 15 minutes, the liquid is kept at a different temperature level than during the hybridization step and is moved with respect to the active surface of the chip shaped carrier in the same way as during the hybridization step.

5) Stain Hybridization

In this step a fluorescent solution is added to the sample containing liquid contained in the cartridge in order that individual fluorescing molecules can get attached to DNA fragments. During this step the cartridge is kept again at a higher temperature level.

6) Stain Rinse

In this step remaining free fluorescing molecules are washed out of the cartridge by means injecting a washing buffer through an inlet of the cartridge at a suitable first position thereof and changing the position cartridge to a second position at which liquid carrying those free fluorescing molecules is withdrawn from the cartridge through an outlet thereof. This step is repeated up to ten times.

7) Detection

After step 6) the sample is bound to the active surface 15 of chip shaped carrier 14, this surface is flooded with a sample-free buffer, and the cartridge containing the sample containing liquid is transferred by suitable transport means which include a gripper to a detection unit, where the active surface of chip shaped carrier is scanned with a laser beam and fluorescent light emerging from said active surface in response to that excitation is measured by means of suitable instrument. In order that this detection can be performed the cartridge has an opening through which the chip shaped carrier and the active surface thereof are accessible to opto-electronic examination.

List of Reference Numbers 11 chamber
12 cartridge
13 channel
14 chip shaped carrier of an array of oligonucleotides
15 active surface of carrier 14
16 cartridge holder
17 pipetting needle
18 level of liquid contained in cartridge 12

19 back side surface of chip shaped carrier 14
21 channel plate
22 chip plate
23 cavity of chip plate
24 inner surface of channel plate
25 inner surface of chip plate
26 first angular position
27 intermediate angular position
28 second angular position
29 angular position of cartridge 12 for effecting a pipetting operation
31 tongue
32 tongue
33 outer surface of chip plate 22
34 outer surface of channel plate 21
35 opening (inlet/outlet)
36 cartridge holder
37 width of end segment of channel 13
38 width of end segment of channel 13
39 width of central part of channel 13
41 sealing frame
42 locking frame
61 motor
62 drive means
63 coupling means
65 transport head
66 gripper
67 pipetting unit
S-S mid-axis of cartridge 12
Z-Z a vertical straight line Modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus and of the method described may be varied without departing from the spirit of the invention and the exclusive use of all modifications which come within the scope of the appended claims is reserved.

The invention claimed is:

1. A system for processing a nucleic acid sample contained in a liquid, said system comprising
    (a) a cartridge which comprises
        (a.1) a chip shaped carrier having an active surface which carries an array of oligonucleotides, said active surface facing an inner surface of a part of said cartridge, and
        (a.2) a chamber having a narrow interior and including a channel, a portion of said channel lying between said active surface and said inner surface,
    (b) a cartridge holder which is adapted to hold said cartridge, and
    (c) means for oscillating said cartridge holder and thereby said cartridge about an axis of rotation which is substantially perpendicular to a vertical plane and thereby moving said cartridge back and forth between a first angular position and a second angular position which lie on opposite sides of an intermediate angular position at which said active surface of said chip shaped carrier is substantially at the lowest part of its motion path caused by said oscillating of the cartridge in order to cause relative motion of the liquid contained in said channel with respect to said active surface of said chip shaped carrier.

2. A system according to claim 1, wherein said channel is a curved channel.

3. A system according to claim 1, wherein said active surface of the chip shaped carrier is adjacent a central portion of said channel.

4. A system according to claim 1, wherein in cartridge holder is designed to hold the cartridge in such a way that said active surface of said chip shaped carrier lies in a substantially vertical plane.

* * * * *